(12) United States Patent
Dambinova

(10) Patent No.: US 8,569,448 B2
(45) Date of Patent: Oct. 29, 2013

(54) NMDAR BIOMARKERS FOR DIAGNOSIS AND TREATMENT OF TRAUMATIC BRAIN INJURY AND OTHER DISORDERS

(75) Inventor: Svetlana A. Dambinova, Atlanta, GA (US)

(73) Assignee: Grace Laboratories, LLC, Atlanta, GA (US)

( * ) Notice: Subject to any disclaimer, the term of this patent is extended or adjusted under 35 U.S.C. 154(b) by 0 days.

(21) Appl. No.: 13/190,271

(22) Filed: Jul. 25, 2011

(65) Prior Publication Data

US 2012/0010147 A1  Jan. 12, 2012

Related U.S. Application Data

(63) Continuation of application No. 12/518,626, filed as application No. PCT/US2007/087290 on Dec. 12, 2007, now abandoned.

(60) Provisional application No. 60/874,458, filed on Dec. 12, 2006.

(51) Int. Cl.
  *A61K 38/00* (2006.01)
  *C07K 16/00* (2006.01)
  *G01N 33/53* (2006.01)

(52) U.S. Cl.
  USPC ........ 530/326; 530/324; 530/300; 530/387.9; 435/7.92; 436/503

(58) Field of Classification Search
  None
  See application file for complete search history.

*Primary Examiner* — Olga N Chernyshev
(74) *Attorney, Agent, or Firm* — Arnall Golden Gregory LLP

(57) ABSTRACT

Provided are methods for detecting various subunits and isoforms of NMDA receptors to help diagnose and differentiate (1) the anatomical location of NMDA receptor over-expression. (2) ischemic conditions in the central and peripheral nervous systems, and (3) the type and cause of chronic pain.

6 Claims, No Drawings

NMDAR BIOMARKERS FOR DIAGNOSIS AND TREATMENT OF TRAUMATIC BRAIN INJURY AND OTHER DISORDERS

RELATED APPLICATIONS

This application is a continuation of U.S. Nonprovisional patent application Ser. No. 12/518,626, filed Jun. 10, 2009, which claims priority to PCT Application No. PCT/US2007/087290, filed Dec. 12, 2007, which claims priority to U.S. Provisional Application No. 60/874,458, filed Dec. 12, 2006.

REFERENCE TO SEQUENCE LISTING

The Sequence Listing submitted Nov. 11, 2011 as a text file named "23431_3_US3_Sequence_Listing.txt," created on Nov. 4, 2011, and having a size of 1.17 kilobytes is hereby incorporated by reference pursuant to 37 C.F.R. §1.52(e)(5).

FIELD OF THE INVENTION

This invention relates to methods of diagnosing and treating brain and spinal cord injury due to trauma, which may lead to secondary cerebral ischemia and epilepsy. The invention also relates to methods of diagnosing and treating peripheral nervous system damage, including neuropathic pain as a consequence of diabetes mellitus and surgery, and to methods for distinguishing peripheral from central neuropathies.

BACKGROUND OF THE INVENTION

Traumatic brain injury (TBI) or neurotrauma contributes to numerous deaths and cases of permanent disability in the United States and world-wide. Of the 1.4 million people who sustain a TBI each year in the United States, 50,000 will die, 235,000 will be hospitalized, and another 1.1 million will be treated and released from an emergency department (Langlois J A, Rutland-Brown W, Thomas K E. Traumatic brain injury in the United States: emergency department visits, hospitalizations, and deaths, Atlanta (Ga.): Centers for Disease Control and Prevention, National Center for Injury Prevention and Control; 2004). Among children ages 0 to 14 years in the United States, TBI results in 435,000 visits to the emergency department each year, 2,685 fatalities, and 37,000 hospitalizations.

Diabetes mellitus is the most common cause of peripheral neuropathy in the United States (Kelkar, Seminars in Neurol, 2005; 25:168-173). Approximately half of all diabetics demonstrate symptoms of neuropathy. The usual clinical pattern is characterized by a slowly progressive mixed sensorimotor and autonomic polyneuropathy. The presence of small-vessel disease in human diabetic nerves suggests that diminished endoneurial blood flow plays a role in human diabetic neuropathy, particularly with respect to scattered infarctions in the proximal regions of peripheral nerves attributable to vasa nervorum inflammatory vasculopathy (Singleton, Seminars in Neurol, 2005; 25:185-195).

Abnormal spiking activity and peripheral neuropathy excitotoxic activation of pre- and postsynaptic NMDA receptors is a key event that triggers downstream pathways implicated in subsequent neuronal death in cases of cerebral ischemia underlying neurotrauma and stroke. Peripheral neuropathy mostly causes damage in pre-synaptical membranes while post-synaptical events imply cerebrovascular system impairment.

The N-methyl-d-aspartate subtype of glutamate receptor (NMDAR or NMDA receptor) serves critical functions in physiological and pathological processes in the central and peripheral nervous system, including neuronal development, plasticity and neurodegeneration. Various investigators have reported that the receptor consists of three primary subunits: NR1, NR2A-D, and NR3A-B, and that the coexpression of NR3A with NR1 and NR2 subunits modulates NMDAR activity in pre- and post-synaptical membranes.

The postsynaptic NR2 subfamily consists of four individual subunits, NR2A to NR2D. In situ hybridization has revealed overlapping but different expression for NR2 mRNA. In particular, NR2A mRNA is distributed ubiquitously like NR1 with highest densities occurring in hippocampal regions. In contrast, NR2B is expressed predominantly in the forebrain but not in the cerebellum where NR2C predominates (Parsons et al., Drug News Perspect. Nov. 1998; 11(9):523-569). The spinal cord reportedly expresses high levels of NR2C and NR2D (Tolle et al., J Neurosci. 1993 December; 13(12):5009-28) and these may form heteroligomeric receptors with NR1 plus NR2A (Sundstrom et al., Exp Neurol. 1997 December; 148(2):407-13).

NR3 is reportedly expressed predominantly in the developing central nervous system and does not seem to form functional homomeric glutamate-activated channels (Sucher et al., J Neurosci. 1995 October; 15(10):6509-20). From in situ and immunocytochemical analyses, it is known that NR3B is expressed predominantly in motor neurons, whereas NR3A is more widely distributed.

Zukin et al. have reported that alternative splicing generates eight isoforms for the pre- and postsynaptic NR1 subfamily (Zukin and Bennett, Trends Neurosci. 1995 July; 18(7):306-13). The variants arise from splicing at three exons; one encodes a 21-amino acid insert in the N-terminal domain (N1, exon 5), and two encode adjacent sequences of 37 and 38 amino acids in the C-terminal domain (C1, exon 21 and C2, exon 22). NR1 variants are sometimes denoted by the presence or absence of these three alternatively spliced exons (from N to C1 to C2). $NR1_{111}$ has all three exons, $NR1_{000}$ has none, and $NR1_{100}$ has only the N-terminal exon. The variants from $NR1_{000}$ to $NR1_{111}$ are alternatively denoted as NMDAR1e, c, d, a, g, f, h and b respectively or NMDAR1-4a, -2a, -3a, -1a, -4b, -2b, -3b and -1b respectively, but the more frequent terminology uses non-capitalized subscripts, which suffices for the most common splice variants, i.e. NR1a ($NR1_{011}$ or NMDAR1A) and NR1b ($NR1_{100}$ or NMDAR1G). NR1a receptors are more concentrated in rostral structures such as the cortex, caudate, and hippocampus, while NR1b receptors are principally found in more caudal regions such as the thalamus, colliculi, locus coeruleus and cerebellum (Laurie et al., Brain Res Mol Brain Res. 1995 August; 32(1):94-108).

The role of NMDA receptors has been explored by numerous investigators. For example, it has been reported that the process of peripheral and central sensitization is maintained, at least theoretically and experimentally, through the excitatory neurotransmitter glutamate, which is believed to be released when the NMDA receptor is activated (Gudin, Medscape Neurology & Neurosurgery 2004). In addition, available evidence suggests that the roles of NMDA receptors differ with respect to the processing of visceral and somatic pain. One set of authors have concluded that NMDA receptors are present in peripheral visceral nerves and may be important in visceral pain processing in the absence of inflammation, thus providing a novel mechanism for development of peripheral sensitization and visceral hyperalgesia (McRoberts et al., Gastroenterology 2001; 120:1737-1748).

In a number of studies, blocking NMDA receptors has been proposed as a preventive treatment for protecting neurons from ischemia (Dugan L L and Kim-Han J S In:Basic Neurochemistry. Siegel et al. Eds, 2006, 7th edition, 559-73). However, blocking NMDA receptors may be detrimental to animals and humans (Davis et al, Stroke 2000; 31:347-354; Ikonomidou et al, Proc. Natl. Acad. Sci. U.S.A. 2000; 97:12885-12890). Moreover, although blocking excitotoxicity of NMDA receptors has proven effective in laboratory models of disease, clinical trials of neuroprotective therapies have generally failed to benefit patients (Lees et al. (2000) Lancet 355:1949-1954). These failures are generally attributed to side effects of glutamate receptor antagonists which may evoke failure of high brain functions (mental disturbances, memory decline and asocial behavior).

Some limited efforts have been made at using natural peptides derived from the brain for treating cerebral ischemic events (Gusev, Skvortsova. Brain Ischemia. NY-Boston-Dordecht-London: Kluwer Academic/Plenum Publishers, 2003; 382). For example, it has been shown in clinical trials that ACTG hormone 4-10 fragment (Semax) drastically improves movement and mental performance in patients who have suffered an acute stroke. Cerebrolyzin, an extract of small peptides from pig brain, has shown positive clinical effect optimizing energetic metabolism of nervous cells and $Ca^{2+}$ homeostasis. It has also been shown that cerebrolysin in a dose of 10 mg daily reduces lipid peroxidation and the accumulation of glutamate receptor antibodies, thereby improving patient memory, speech and psychological activity (www.consilium-medicum.com).

Recently, NMDAR peptides and their antibodies have been proposed for the treatment of stroke and epilepsy (During et al, Science, 2000, 287:1453-60) and as biomarkers of neurotoxicity underlying cerebral ischemia and stroke (Dambinova S A, et al. Stroke 2002; 33:1181-1182; Dambinova S A, et al. Clin Chem 2003; 49:1752-1762). With neuronal death or ischemia, NR2 peptide fragments of the NMDA receptor break off and appear in the bloodstream and generate an antibody response. Dambinova et al, have reported that the peptide fragments and antibodies can both be detected in blood samples (Dambinova S A, et al. Stroke 2002). They have further reported that adult patients who have suffered an acute ischemic stroke have elevated blood levels of NR2 peptide/Ab that correlate with the amount of brain damage revealed through brain scans (MRI) and neurocognitive testing (Dambinova S A, et al. Clin Chem 2003; 49:1752-1762).

OBJECTS OF THE INVENTION

It is an object of the present invention to identify the anatomical location of NMDAR over-expression in a human, based on the subunit or isoform of NMDAR that is detected.

It is another object of the invention to provide methods and markers for determining whether pain and other neuropathies (chronic or acute) is due to inflammation or ischemic lesions in the peripheral nervous system, or to trauma to the PNS such as spinal cord injury or trauma to the CNS such as traumatic brain injury.

A still further object of the invention is to distinguish between types and sources of pain based on over-expression of the NMDA receptor, and the NMDA receptor subunit/isoform detected in the bloodstream.

Yet another object is to provide therapies that are useful for treating and preventing ischemic lesions in the peripheral nervous system and chronic pain based on the results of NMDAR detection and quantification in bodily fluids.

SUMMARY OF THE INVENTION

The present invention provides strategies for diagnosing and treating microvascular events in the central and peripheral nervous systems that are caused by trauma to the brain or spinal cord, or impairment of the peripheral nervous system. Secondary ischemic events are often an early consequences of TBI, which may subsequently be followed by epilepsy. The inventors have discovered a role that NMDA receptors play in traumatic brain and spinal cord injuries, and discovered that these injuries give rise to detectable levels of particular NMDA markers in the bloodstream. In particular, the inventors have determined that TBI and spinal cord injuries often give rise to secondary ischemic events and, if not treated properly, may often lead to epilepsy. The markers developed by the inventors are probative of these secondary and downstream events.

The inventors have further determined the involvement of NMDAR markers in the inception and control of peripheral pain and other peripheral neuropathies, and have identified NMDAR markers that are specific for these patterns of NMDAR expression in the peripheral system. Based upon these discoveries, the inventors have developed methods and strategies for distinguishing between central and peripheral neuropathies, and the anatomical source of the neuropathy.

In essence, the inventors have discovered that particular recombinant and/or mutant NR1 and NR2 peptides are over-expressed in different anatomical regions of the human body (Table 1), and that when these subunits are over-expressed they are protcolysed into peptide fragments that enter the bloodstream and are recognized as foreign antigens by the immune system, which responds by generating detectable amounts of autoantibodies. The existence and location of NMDAR over-expression in the human body can thus be ascertained by detecting NMDAR isoform fragments or antibodies in bodily fluids such as the bloodstream, and by determining the particular subunit or isoform of NMDAR that is present.

Still other embodiments pertain to a novel peptide developed by the inventors for selectively antagonizing NMDAR activity, defined by chemical structure (I): Glu-X-Glu, wherein (a) Glu is the residue of glutamic acid; and (b) X is a chain comprising from two to ten amino acid residues and an optional chelating agent selected from magnesium, iron and zinc. In one embodiment the invention provides methods for antagonizing NMDAR activity by administering a compound defined by chemical structure (I). In other embodiments the invention provides pharmaceutical compositions that contain the compound defined by chemical structure (I).

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Definitions and Use of Terms

As used in this specification and in the claims which follow, the singular forms "a," "an" and "the" include plural referents unless the context clearly dictates otherwise. Thus, for example, reference to "a fragment" includes mixtures of fragments, reference to "an cDNA oligonucleotide" includes more than one oligonucleotide, and the like.

"Polypeptide," "protein" and "peptide" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications (isoforms) of the polypeptide, for example, glycosylations, acetylations, phosphorylations, chelates, and the like. In addition, protein fragments, analogs, mutated or variant proteins, chimeric peptides and the like are included within the meaning of polypeptide. The polypeptide, protein and peptides may be in cyclic form or they may be in linear form. In one particular embodiment, the peptides of the current invention are deglycosylated, or dephosphorylated from their natural state, or are prepared synthetically without naturally occurring glycosylation or phosphorylation.

An NMDA receptor or NMDAR is one of a family of ligand-gated ion channels that bind preferentially to N-methyl-D-aspartate and that mediate the vast majority of excitatory neurotransmission in the brain (Dingledine R. et al., Pharmacol Rev. 1999 March; 51(1):7-61.). The receptors include subunits reported in the literature as NR1, NR2A, NR2B, NR2C, NR2D, NR3A and NR3B, that perform distinct pharmacological functions. GenEMBL Accession Nos. have been reported for NR1 (X58633), NR2A (U09002) and NR2B (U28861), and are described in WO 02/12892 to Dambinova.

An NMDA receptor peptide refers to a full length NMDA receptor protein, a peptide fragment of the naturally or synthetically occurring full length NMDA receptor, or an anologue or isoform thereof. An NR2 peptide thus includes the full length NR2A, NR2B, NR2C and NR2D subunits, in addition to fragments, analogs and derivatives thereof. Similarly, an NR2A, NR2B, NR2C, or NR2D peptide means the full length naturally occurring NR2A, NR2B, NR2C or NR2D peptide subunits, or a fragment, analog or derivative thereof. The N-terminal domain of NMDA peptides refers to the amino acid N-terminal domain fragment of the full length peptide, or a fragment, analog or derivative thereof, typically about 40 or 50 amino acids long, but as much as 150, 200 or 300 amino acids long, as described in WO 02/12892 to Dambinova.

As used herein, the terms "antagonist" and "natural peptide containing zinc, $Fe^{3+}$ and or magnesium," when used in the context of modulating a binding interaction (such as the binding of a glutamate, glycine and polyamine domain sequences to the N-terminal fragment of natural or synthetic NMDA receptor sequence), are used interchangeably and refer to an agent that reduces the binding of the, e.g., N-terminal fragment of natural or synthetic NMDA receptor sequence and the, e.g., domain peptide.

An "analogue" of a peptide means a peptide that contains one or more amino acid substitutions, deletions, additions, or rearrangements. For example, it is well known in the art of protein biochemistry that an amino acid belonging to a grouping of amino acids having a particular size or characteristic (such as charge, hydrophobicity, and hydrophilicity) can often be substituted for another amino acid without altering the activity of the protein, particularly in regions of the protein that are not directly associated with biological activity. Thus, an analogue of an NMDA peptide is useful in the present invention if it includes amino acid substitutions, deletions, additions or rearrangements at sites such that antibodies raised against the analogue are still specific against the NMDAR peptide.

Unless stated to the contrary, an NMDAR analogue or mutant as used in this document refers to a sequence that has at least 80% amino acid identity with naturally occurring NMDA, although it could also contain at least 85%, 90%, or 95% identity. Amino acid identity is defined by an analogue comparison between the analogue or mutant and naturally occurring NMDA. The two amino acid sequences are aligned in such a way that maximizes the number of amino acids in common along the length of their sequences; gaps in either or both sequences are permitted in making the alignment in order to maximize the number of common amino acids. The percentage amino acid identity is the higher of the following two numbers: (1) the number of amino acids that the two peptides have in common with the alignment, divided by the number of amino acids in the NMDA analogue, multiplied by 100, or (2) the number of amino acids that the two peptides have in common with the alignment, divided by the number of amino acids in naturally occurring NMDA peptide, multiplied by 100. Amino acids appended to the ends of the fragment under analysis are not taken into consideration.

NMDA derivatives include naturally occurring NMDA and NMDA analogues and fragments thereof that are chemically or enzymatically derivatized at one or more constituent amino acids, including side chain modifications, backbone modifications, and N- and C-terminal modifications, by for example acetylation, hydroxylation, methylation, amidation, phosphorylation or glycosylation. The term also includes NMDA salts such as zinc NMDA and ammonium NMDA.

A protein or peptide is measured "directly" in the sense that the protein or peptide is itself measured in the biological sample, as opposed to some other indirect measure of the protein or peptide such as autoantibodies to the protein or peptide, or cDNA or mRNA associated with the expression of the protein or peptide.

The term "antibody" is synonymous with "immunoglobulin." As used herein, the term "antibody" includes both the native antibody, monoclonally generated antibodies, polyclonally generated antibodies, recombinant DNA antibodies, and biologically active derivatives of antibodies, such as, for example, Fab', $F(ab')_2$ or Fv as well as single-domains and single-chain antibodies. A biologically active derivative of an antibody is included within this definition as long as it retains the ability to bind the specified antigen. Thus, an NR2 antibody that binds specifically to an NR2 peptide has the ability to bind at least one NR2 peptide. In one particular embodiment, the immunoglobulins of the current invention are deglycosylated or dephosphorylated from their natural state, or are prepared synthetically without naturally occurring glycosylation or phosphorylation.

When ranges are given by specifying the lower end of a range separately from the upper end of the range, it will be understood that the range can be defined by selectively combining any one of the lower end variables with any one of the upper end variables that is mathematically possible.

Discussion

All of the strategies developed by the inventors are based on the discovery of novel NMDAR isoforms released to the bloodstream, and the location in the human body where particular NMDAR isoforms are expressed. NMDAR isoforms have been revealed by HPLC (on the basis of different retention time), electrofocusing (various protein p1) and immunoblot of peptides using monoclonal antibodies to phosphorylated or acetylated isoform peptide fragments. Glutamate receptor isoforms targeted by this invention include recombinant and/or mutant subtypes that are optionally modified through acetylation or phosphorylation.

In a first principal embodiment the invention provides methods and kits for determining the anatomical source of NMDAR isoform expression in the human body, and the pathological process leading to such over-expression. The location of such over-expression, the pathological process leading to such over-expression, the diseased state associated with such over-expression, and the particular NMDAR isoform that is over-expressed, are all described in greater detail in Table 1. The markers can be used to distinguish between any of the tissues, processes, or disease states identified in Table 1.

TABLE 1

Source of Recombinant and/or Mutant NMDAR

| NMDAR Isoform | Tissue | Process | Disease |
|---|---|---|---|
| NR1A/NR1B | Platelets | Inflammation | Peripheral neuropathy; diabetic neuropathy |
| NR1/NR2 | Spinal cord, brain | Ischemic lesion | Traumatic spinal cord injury; brain trauma; central neuropathy |

Peripheral and central neuropathies as used herein shall be understood to include neuropathic pain.

The terminology employed in this document is designed to describe recombinant isoforms. Thus, for example, an NR1/NR2 peptide refers to a peptide that combines sequences from the NR1 NMDA receptor subtype, and the NR2 NMDA receptor subtype. The sequences are preferably autoantigenic, and preferably derive from the N-terminal domain of the recited NMDA receptor subtype. The peptides are preferably less than about 100, 60 or 40 amino acids in length, and greater than about 10, 15 or 20 amino acids. It will of course be understood that analogs of such sequences may also be present in the recombinant peptide.

A particularly useful embodiment involves the detection or measurement of both NR1A/NR1B and NR1/NR2, insofar as the results can be used to distinguish between central neuropathy or pain, especially neuropathies and pain deriving from traumatic brain or spinal cord injury (when NR1/NR2 is measured above a designated standard or otherwise detected) and peripheral neuropathy or pain (when NR1A/NR1B is measured above a designated standard or otherwise detected). Therefore, in one embodiment the invention provides a method of diagnosing NMDAR over-expression in a human subject comprising:

a) testing in a bodily fluid, directly or indirectly, the amount of one or more recombinant NMDAR peptide fragments selected from:
   i) an NR1A/NR1B recombinant peptide or analog thereof; and
   ii) an NR1/NR2 recombinant peptide or analog thereof;
b) optionally comparing said amounts of NMDAR peptide fragments with designated standards for said recombinant NMDAR peptide fragments; and
c) optionally correlating an excess amount of one or more recombinant NMDAR peptide fragments with an anatomical location of NMDAR over-expression in the patient.

In one embodiment the invention provides a method of diagnosing a patient suspected of suffering from diabetic or peripheral neuropathy or pain comprising: (a) directly or indirectly testing a biological fluid from said patient for an amount of NR1A/NR1B recombinant peptide or an analog thereof; and (b) optionally comparing said amount of NR1A/NR1B recombinant NMDAR peptide with a designated standard for said recombinant NMDAR peptide; and (c) optionally correlating an excess amount of said NR1A/NR1B recombinant peptide or analog thereof with diabetic or peripheral neuropathy or pain, or NMDAR over-expression in blood platelets.

In another embodiment the invention provides a method of diagnosing a patient suspected of suffering from traumatic brain or spinal cord injury, or central neuropathy or pain, comprising: (a) directly or indirectly testing a biological fluid from said patient for an amount of NR1/NR2 recombinant peptide or an analog thereof; and (b) optionally comparing said amount of NR1/NR2 recombinant NMDAR peptide with a designated standard for said recombinant NMDAR peptide; and (c) optionally correlating an excess amount of said NR1/NR2 recombinant peptide or analog thereof with NMDAR over-expression in the spinal cord or brain, or central neuropathy or pain, or an ischemic lesion in the spinal cord or brain.

Said designated standard for NR1A/NR1B preferably refers to a population norm in apparently healthy human subjects, or a previously recorded value of NR1A/NR1B for said patient. Alternatively, said designated standard may simply refer to a non-detectable quantity of peptide or analog thereof. Population norms for NR1A/NR1B peptides range generally from 0.01 to 1.0 ng/ml of plasma and a cutoff may be selected from any figure between these two endpoints including 0.01, 0.025, 0.05, 0.075, 0.1, 0.25, 0.5, 0.75 or 1.0 ng/ml of plasma. Population norms for antibodies specific for NR1A/NR1B peptides generally range from 0.1 to 10.0 ng/ml of plasma, and a cutoff may be selected from any figure between these two endpoints including 0.1, 0.25, 0.5, 0.75, 1.0, 2.5, 5.0, 7.5 or 10.0 ng/ml of plasma.

Said designated standard for NR1/NR2 preferably refers to a population norm in apparently healthy human subjects, or a previous recorded value of NR1/NR2 for said patient. Alternatively, said designated standard may simply refer to a non-detectable quantity of peptide or analog thereof. Population norms for NR1/NR2 peptides range generally from 0.01 to 1.0 ng/ml of plasma and a cutoff may be selected from any figure between these two endpoints including 0.01, 0.025, 0.05, 0.075, 0.1, 0.25, 0.5, 0.75 or 1.0 ng/ml of plasma. Population norms for antibodies specific for NR1/NR2 peptides generally range from 0.1 to 10.0 ng/ml of plasma, and a cutoff may be selected from any figure between these two endpoints including 0.1, 0.25, 0.5, 0.75, 1.0, 2.5, 5.0, 7.5 or 10.0 ng/ml of plasma.

Still other embodiments pertain to the use of these receptors and their biological markers in diagnostic kits, and to the use of the markers in diagnosing various pathological conditions and anatomical locations associated with over-expression of NMDA receptors. Such methods are preferably carried out by measuring recombinant or mutant peptides, and are preferably carried out through the use of a kit that allows one to test for the recombinant or mutant peptides.

In another embodiment the invention provides a kit comprising recombinant NMDAR peptide fragments, or antibodies that specifically bind to recombinant NMDAR peptide fragments, or nucleic acids that encode recombinant NMDAR peptide fragments, each bound to a diagnostic substrate or indicator reagent, wherein said recombinant NMDAR peptide fragments are selected from:

a) an NR1A/NR1B recombinant peptide or analog thereof; and b) an NR1/NR2 recombinant peptide or analog thereof, or a combination thereof.

In still another embodiment, the invention provides an isolated recombinant or mutant NMDAR peptide, or an isolated antibody specific for said recombinant or mutant NMDAR peptide, wherein said recombinant or mutant peptide is selected from:
a) an NR1A/NR1B recombinant peptide or analog thereof; and
b) an NR1/NR2 recombinant peptide or analog thereof.

In another embodiment the invention provides an isolated antibody that is specific for the above-mentioned recombinant peptides (a)-(b), or a nucleic acid that encodes the recombinant peptides. In still another embodiment the peptide, antibody or nucleic acid is bound to a diagnostic substrate or an indicator reagent.

The term "isolated" excludes instances wherein the peptide or antibody may have been separated from other peptide bands, as in gel electrophoresis, but the peptide or antibody has not been physically isolated from the gel or the other peptide bands. The peptide can, of course, be part of a much larger peptide, as contemplated by the "comprising" terminology. In a preferred embodiment, however, the peptide is exactly as represented, or an analog thereof, optionally bound through an appropriate linker to a diagnostic substrate (such as a plate, a particle or a bead) or to an indicator reagent. Similarly, the antibodies and nucleic acids of the present invention are preferably specific for the exact sequences represented (or analogs thereof), and are optionally bound through an appropriate linker to a diagnostic substrate or an indicator reagent.

Preferred amino acid sequences for the recombinant NMDAR peptides discussed above are set forth below in Table 2.

TABLE 2

NMDA Receptor Isoforms

| NMDAR Isoform | Amino Acid Sequences |
| --- | --- |
| NR1A/NR1B | RVEFNEDGDRKVNSEEEEEDALT 23 (SEQ ID 1) |
|  | RVEFNEDGDRLEKENITDPPRGCVGN 26 (SEQ ID 2) |
| NR1/NR2 | RVEFNEDGDRSYIPEAKASCYG 22 (SEQ ID 3) |

Therefore, in a first principal embodiment, the invention provides an isolated peptide comprising SEQ ID 1, SEQ ID 2, or SEQ ID 3, or an analog thereof. In a second principal embodiment the invention provides an isolated antibody that is specific for, or a nucleic acid that encodes, SEQ ID 1, SEQ ID 2, or SEQ ID 3, or an analog thereof (i.e. of such sequence). In still another embodiment the peptide, antibody or nucleic acid is bound to a diagnostic substrate or an indicator reagent.

The methods of the present invention can be performed using practically any biological fluid where circulating cerebral NMDA receptors, or markers of such receptors, are expressed or found, including blood, urine, blood plasma, blood serum, cerebrospinal fluid, saliva, perspiration or brain tissue. In a preferred embodiment the biological fluid is plasma or serum, and in an even more preferred embodiment the plasma or serum is diluted to a ratio of about 1:50.

In yet another embodiment the invention provides novel compounds that are useful for antagonizing NMDAR over-expression, especially NMDAR over-expression in the brain induced by ischemic events. These novel compounds can be defined by the chemical structure (I):

Glu-X-Glu                        (I)

wherein: Glu is the residue of glutamic acid; and X is a chain comprising from two to ten amino acid residues and an optional chelating agent selected from magnesium, iron and zinc.

In a preferred embodiment, —X— is represented by chemical structure (II):

-A-B-C-                             (II)

wherein A and C are independently residues of lysine, glycine, arginine, taurine and glutamine; and B is a chain comprising from zero to eight amino acids and a chelating agent selected from magnesium, iron and zinc. In a particularly preferred embodiment, A and C are independently residues of lysine and arginine; and B is a metal chelating agent.

In another embodiment the invention provides a pharmaceutical composition comprising the novel compounds of the present invention, in an amount sufficient to antagonize NMDAR activity, in combination with a pharmaceutically acceptable excipient. In still another embodiment the invention provides a method of antagonizing NMDAR activity comprising administering to a human a pharmaceutical composition comprising the novel compounds of the present invention, in an amount sufficient to antagonize NMDAR activity. In a particularly preferred embodiment, the patient is diagnosed as suffering from chronic or acute pain or diabetic neuropathy.

Suitable doses range from about 0.01 to about 10.0 mg/day, 0.05 to about 1.0 mg/day, and from about 0.1 to about 0.5 mg/day. The dose may be administered once, twice or even three times per day, and is preferably administered until a desired level of clinical improvement is observed in the patient to whom the drug is administered.

The compound may be prepared by numerous methods known in the art to synthetic chemists for making and purifying amino acid chelates. Methods are taught, for example, in U.S. Pat. Nos. 4,830,716 and 4,599,152. For example, pharmaceutical grade amino acid and peptide chelates, free of interfering anions, can be made by reacting one or more amino acid or peptides with a metal member selected from the group consisting of elemental metals, metal oxides, metal hydroxides and metal carbonates in an aqueous environment employing at least a two fold molar excess of amino acid or peptide relative to the metal. The reaction may be carried out in the presence of non-interfering anions such as anions from citric acid, ascorbic acid, acetic acid, carbonic acid and ammonium and alkali metal salts thereof. Where the molecule desired is not perfectly symmetrical (i.e. when there are two different peptides or amino acids chelated to the metal), it will be necessary to separate the desired product from the reaction mixture, and such separation can be performed using conventional techniques such as high performance liquid chromatography. Separation methods are taught, for example, in Tommel D K L et al, A method for the separation of peptides and α-amino acids; Biochem J. 1968 April; 107 (3): 335-340, and Hill-Cottingham D G et al., Analysis of iron chelates in plant extracts; J Sci of Food and Agr. 2006; 12(1): 69-74

Treatment Platform

The compounds of the invention may be administered to a subject per se or in the form of a sterile composition or a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the active peptides or peptide analogues into preparations which can be used pharmaceutically. Proper formulation is dependent upon the route of administration chosen.

For topical administration the compounds of the invention can be formulated as solutions, gels, ointments, creams, suspensions, etc. as are well-known in the art. Systemic formulations include those designed for administration by injection, e.g. subcutaneous, intravenous, intramuscular, intranasal, intrathecal or intraperitoneal injection, as well as those designed for transdermal, transmucosal, oral or pulmonary administration.

For injection, the compounds of the invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents. Alternatively, the compounds can be in powder form for constitution with a suitable vehicle, e.g., sterile pyrogen-free water, before use.

For oral administration or vaccination, the compounds can be readily formulated by combining the active peptides (antibodies) or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semi-permeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The compounds of the invention will generally be used in an amount effective to achieve the intended purpose (e.g., treatment of central or peripheral neuronal injury). The therapies of the invention are performed by administering the subject drug in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein. An "therapeutic amount" or "therapeutic concentration" of a NMDAR isoforms or antibodies is an amount that reduces binding activity to receptor by at least about 40%, preferably at least about 50%, often at least about 70%, and even as much as at least about 90%. Binding can be measured in vitro (e.g., in an assay) or in situ.

For systemic administration, a therapeutically effective dose can be estimated initially from in vitro assays. For example, a dose can be formulated in animal models to achieve a circulating concentration range that includes the IC50. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. Usual patient dosages for administration by injection range from about 0.1 to 10 mg/day, preferably from about 0.5 to 1 mg/day. Therapeutically effective serum levels may be achieved by administering multiple doses each day. For usual peptide/antibodies therapeutic treatment of cerebral ischemic events within 6 hours of event is typical.

In cases of local, administration or selective uptake, the effective local concentration of the compounds may not be related to plasma concentration and should be optimized therapeutically effective local dosages without undue experimentation. The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. Preferably, a therapeutically effective dose of the compounds described herein will provide therapeutic benefit without causing substantial toxicity.

Toxicity of the compounds described herein can be determined by standard pharmaceutical procedures in experimental animals, e.g., by determining the LD50 (the dose lethal to 50% of the population) or the LD100 (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

Diagnostic Platforms

The diagnostic methods of the present invention can be performed using any number of known diagnostic techniques, including direct or indirect ELISA, RIA, immunodot, immunoblot, latex agglutination, lateral flow, fluorescence polarization, and microarray. In one particular embodiment, the invention is practiced using an immobilized solid phase for capturing and measuring the NMDAR peptide marker. Therefore, in one embodiment the methods of the invention comprise: (a) contacting a biological sample from the patient with an immobilized solid phase comprising a NMDAR peptide or antibody, for a time sufficient to form a complex between said NMDAR peptide or antibody and NMDAR antibody or peptide in said biological sample; (c) contacting said complex with an indicator reagent attached to a signal-generating compound to generate a signal; and (d) measuring the signal generated. In a preferred embodiment, the indicator reagent comprises chicken anti-human or anti-human IgG attached to horseradish peroxidase.

In a preferred embodiment, the solid phase is a polymer matrix. More preferably, the polymer matrix is polyacrylate, polystyrene, or polypropylene. In one preferred embodiment the solid phase is a microplate. In another preferred embodiment, the solid phase is a nitrocellulose membrane or a charged nylon membrane.

In another embodiment, the method is performed using agglutination. Therefore, in still another embodiment the invention comprises: (a) contacting a biological sample from the patient with an agglutinating carrier comprising a NMDAR peptide or antibody, for a time sufficient to form an agglutination complex between said NMDAR peptide or antibody and NMDAR antibody or peptide in said biological sample; (c) generating a signal from the agglutination; (d) correlating said signal to said levels of one or more markers of NMDAR peptide or antibody. In a preferred embodiment, the "sufficient time" is less than 30, 20, 15 or even 10 minutes.

Latex agglutination assays have been described in Beltz, G. A. et al., in Molecular Probes: Techniques and Medical Applications, A. Albertini et al., eds., Raven Press, New York, 1989, incorporated herein by reference. In the latex agglutination assay, antibody raised against a particular biomarker is immobilized on latex particles. A drop of the latex particles is added to an appropriate dilution of the serum to be tested and mixed by gentle rocking of the card. With samples lacking sufficient levels of the biomarkers, the latex particles remain in suspension and retain a smooth, milky appearance. However, if biomarkers reactive with the antibody are present, the latex particles clump into visibly detectable aggregates.

An agglutination assay can also be used to detect biomarkers wherein the corresponding antibody is immobilized on a suitable particle other than latex beads, for example, on gelatin, red blood cells, nylon, liposomes, gold particles, etc. The presence of antibodies in the assay causes agglutination, similar to that of a precipitation reaction, which can then be detected by such techniques as nephelometry, turbidity, infrared spectrometry, visual inspection, colorimetry, and the like.

The term latex agglutination is employed generically herein to refer to any method based upon the formation of detectable agglutination, and is not limited to the use of latex as the immunosorbent substrate. While preferred substrates for the agglutination are latex based, such as polystyrene and polypropylene, particularly polystyrene, other well-known substrates include beads formed from glass, paper, dextran, and nylon. The immobilized antibodies may be covalently; ionically, or physically bound to the solid-phase immunoadsorbent, by techniques such as covalent bonding via an amide or ester linkage, ionic attraction, or by adsorption. Those skilled in the art will know many other suitable carriers for binding antibodies, or will be able to ascertain such, using routine experimentation.

Conventional methods can be used to prepare antibodies for use in the present invention. For example, by using a peptide of a NMDA protein, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be administered and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for NMDAR proteins or fragments as described herein.

In one embodiment the method is practiced using a kit that has been calibrated at the factory based upon antibodies purified from human blood. Therefore, in another embodiment the invention is practiced under the following conditions: (a) NMDAR antibody levels in said biological fluid are measured using a diagnostic kit; (b) said diagnostic kit comprises bound NMDAR peptides; and (c) said kit is manufactured against an antibody standard comprising a fraction of immunoglobulins G purified from human blood.

In addition, the method can be practiced using commercially available chemiluminescence techniques. For example, the method could employ a two-site sandwich immunoassay using direct chemiluminescent technology, using constant amounts of two monoclonal antibodies. The first antibody, in a fluid reagent, could be an acridinium ester labeled monoclonal mouse anti-human NMDA receptor peptide BNP (F(ab')$_2$ fragment specific to a first portion of the peptide. The second antibody, in the solid phase, could be a biotinylated monoclonal mouse anti-human antibody specific to another portion of the peptide, which could be coupled to streptavidin magnetic particles. An immuno-complex would be formed by mixing a patient sample and the two antibodies. After any unbound antibody conjugates are washed away, the chemiluminescence of the immuno-complex signal could then be measured using a luminometer.

When the NMDA receptors are detected indirectly, by measuring the cDNA expression of the NMDA receptors, the measuring step in the present invention may be carried out by traditional PCR assays such as cDNA hybridization, Northern blots, or Southern blots. These methods can be carried out using oligonucleotides encoding the polypeptide antigens of the invention. Thus, in one embodiment the methods of this invention include measuring an increase of NMDAR cDNA expression by contacting the total DNA isolated from a biological sample with oligonucleotide primers attached to a solid phase, for a sufficient time period. In another preferred embodiment, NMDAR cDNA expression is measured by contacting an array of total DNA bound to a solid matrix with a ready-to-use reagent mixture containing oligonucleotide primers for a sufficient time period. Expressed NMDAR cDNA is revealed by the complexation of the cDNA with an indicator reagent that comprises a counterpart oligonucleotide to the cDNA attached to a signal-generating compound. The signal-generating compound is preferably selected from the group consisting of horseradish peroxidase, alkaline phosphatase, urinase and non-enzyme reagents. The signal-generating compound is most preferably a non-enzyme reagent.

The immunosorbent of the present invention for measuring levels of autoantibody can be produced as follows. A fragment of the receptor protein is fixed, preferably by covalent bond or an ionic bond, on a suitable carrier such as polystyrene or nitrocellulose. If the standard polystyrene plate for immunological examinations is employed, it is first subjected to the nitration procedure, whereby free nitrogroups are formed on the plate surface, which are reduced to amino groups and activated with glutaric dialdehyde serving as a linker. Next the thus-activated plate is incubated with about 2 to 50 nM of the target peptide for the purpose of chemically fixing the respective immunogenic fragment of the receptor protein for a time and at a temperature sufficient to assure fixation (i.e. for about 16 hours at 4° C.).

It is also practicable to produce the immunosorbent by fixing the respective fragment of the receptor protein on nitrocellulose strips by virtue of ionic interaction. The respective fragment of the receptor protein isolated from the mammals' brain is applied to nitrocellulose and incubated for 15 min at 37° C. Then nitrocellulose is washed with a 0.5% solution of Tween-20, and the resultant immunosobent is dried at room temperature and stored in dry place for one year period.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are pans by weight, temperature is in ° C. or is at room temperature, and pressure is at or near atmospheric.

Example 1

NMDA Receptor Peptide and Antibodies as Biomarkers of Ischemic Conditions Underlying Mild Traumatic Brain Injury Mild traumatic brain injury (MTBI) is the most prevalent form of head injury in the US civilian and military settings and poses difficult diagnostic challenges. NMDA receptors involve an apoptotic cascade of cerebral ischemic events on early stage of MTBI. Excessive amounts of NMDA receptors undergo cleavage by serine proteases and peptide fragments enter in the blood stream through compromised BBB. These peptide fragments act as foreign antigens generating antibodies that correlate with progressing ischemic damage and can be measured in the blood. NR1/NR2 peptide/antibodies were evaluated by rapid blood assays in animals and humans.

Sprague-Dawley rats (n=60) subjected to cortical impact (weight-drop method with the force of cortical impact was 20±2.8 g) were tested for spatial leaning using the Morris water maze (MWM) and were sacrificed at 0, 2, 8, 24 d, 3 d, and 7 d. One hundred and seventy three persons with mild neurotrauma were clinically examined at the Military Medical Academy (St. Petersburg, Russia) using Mini Mental State Examination (MMSE) scores with the area of brain damage defined by DWI/MRI. NR1/NR2 peptide/antibodies were measured by fast ELISA in all blood samples.

Impacted rats exhibited impaired spatial learning performance during place trials in MWM. In the blood of rats with mild injury, the level of NR1/NR2 peptide was significantly increased from 6 to 24 hours, while NR1/NR2 antibodies were elevated from 72 h after cortical impact. Of the 173 patients with mild neurotrauma, 121 (70%) had high NR2 peptide content and 25 (14%) showed increased NR1/NR2 antibodies compared with the control level for healthy persons (n=64). Decreased MMSE component scores ($P<0.01$) for orientation, attention and recall were associated with cerebral ischemic events defined by DWI/MRI.

Metabolic changes of NMDA receptor biomarkers that occur in animal models are analogue to alterations in human studies. MTBI leads to cognitive decline due cerebral ischemia. NR2 peptide/antibodies may be helpful in identifying patients with early ischemic events following mild neurotrauma. Rapid blood tests detecting NR1/NR2 peptide/antibodies allow diagnosis and predict consequences of MTBI and would be beneficial to healthcare.

Example 2

NMDA Receptors Isoforms for Signal Trunsduction Improvement in Ischemic Conditions Several double derivatives of glutamic acid {E-(CH$_2$)n-E} or containing amino acids (glycine, lysine, histidine, and/or arginine, {E-amino acid-E}) including chelates (Fe2+, Mg2+, or Zn2+) were synthesized and used to study their physiological functions in isolated giant neurons of mollusk *Planorbarius Corneus*. Application of doubled derivatives evoked neuronal depolarization, while injection of glutamate elicited biphasic responses. This means that the double derivatives of the present invention possess an antagonistic effect on the NMDA binding site. The effect of these substances depended on the length of the amino acid chain (CH2)n between the residues of glutamic acid. The maximal effect was observed in the substance with n=8 and with peptide (glutamic acid-lysine Zn2+-arginin-glutamic acid). Changes in membrane conductance were shown to depend on the type of stereo conformation of these derivatives.

The Hill coefficient (nH) is a central parameter in the study of ligand-protein interactions, which measures the degree of co-operativity between subunits that bind the ligand in multi-subunit proteins. The most common usage of nH is as an estimate of the minimal number of interacting binding sites in positively co-operating systems. The Hill coefficient for tested compounds was about 0.75. It shows the negative cooperativity between double derivatives and NMDAR when binding rises fast initially at low concentrations of ligand and then slows dramatically with small response in respect to increased amounts of the ligand.

The peptide {glutamic acid-lysine Zn2+-arginin-glutamic acid} was injected initially into the left lateral cerebral ventricle at a dose of 1-5 µg (0.1-0.5 µg/µl×10 µl) to rats before middle cerebral artery ligation. The peptide potently protected the cerebral hemispheres from damage induced by MCA occlusion, with rats receiving the treatment suffering 40-45% less cerebral infraction than sham operated placebo rats.

Example 3

Clinical Studies Involving Glutamic Acid-Lysine Zn2+-Arginin-Glutamic Acid Administered Intra-Nasally A clinical study was undertaken to measure the neuroprotective effectiveness of glutamic acid-lysine Zn2+-arginin-glutamic acid in patients diagnosed as suffering a cerebrovasular accident (CVA) or a transient ischemic attack (TIA), based on the existence of confusion, dizziness, facial weakness and lack of balance.

Of 114 patients, 81 were diagnosed as suffering a CVA; 33 were diagnosed as suffering a TIA. Forty CVA patients received placebo while 41 CVA and 33 TIA patients received glutamic acid-lysine Zn2+-arginin-glutamic acid intra-nasally in a saline solution at a dose of 0.1 mg per day, for a period of five days. Patients in the active arm of the trial saw an increase in total MMSE scores of from 25 to 30 when compared to placebo.

A randomized, double-blinded placebo-controlled study was undertaken to evaluate the safety and efficacy of glutamic acid-lysine Zn2+-arginin-glutamic acid administered intra-nasally in a saline solution at a dose of 0.5 mg/day, in 142 patients who had suffered an acute ischemic stroke within the previous six hours. Forty two patients received placebo, 48 received glutamic acid-lysine Zn2+-arginin-glutamic acid (intranasal), and 51 received glycine 2.0 g/day (sublingual), for five consecutive days. The glutamic acid-lysine Zn2+-arginin-glutamic acid treatment decreased 30 day mortality by 23% compared to glycine treatment; the glycine treatment decreased 30 day mortality by 20% when compared to placebo.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

The invention claimed is:

1. An isolated peptide comprising the amino acid sequence of SEQ ID: 1.

2. An isolated peptide comprising the amino acid sequence of SEQ ID: 2.

3. An isolated peptide comprising the amino acid sequence of SEQ ID: 3.

4. The peptide of claim 1 linked to a diagnostic substrate or indicator reagent.

5. The peptide of claim 2 linked to a diagnostic substrate or indicator reagent.

6. The peptide of claim 3 linked to a diagnostic substrate or indicator reagent.

* * * * *

SEQUENCE LISTING

<160> NUMBER OF SEQ ID NOS: 3

<210> SEQ ID NO 1
<211> LENGTH: 23
<212> TYPE: PRT
<213> ORGANISM: Unknown
<220> FEATURE:
<223> OTHER INFORMATION: mammal

<400> SEQUENCE: 1

Arg Val Glu Phe Asn Glu Asp Gly Asp Arg Lys Val Asn Ser Glu Glu
1               5                   10                  15

Glu Glu Glu Asp Ala Leu Thr
            20

```
-continued

<210> SEQ ID NO 2
<211> LENGTH: 26
<212> TYPE: PRT
<213> ORGANISM: Unknown
<220> FEATURE:
<223> OTHER INFORMATION: mammal

<400> SEQUENCE: 2

Arg Val Glu Phe Asn Glu Asp Gly Asp Arg Leu Glu Lys Glu Asn Ile
1               5                   10                  15

Thr Asp Pro Pro Arg Gly Cys Val Gly Asn
            20                  25

<210> SEQ ID NO 3
<211> LENGTH: 22
<212> TYPE: PRT
<213> ORGANISM: Unknown
<220> FEATURE:
<223> OTHER INFORMATION: mammal

<400> SEQUENCE: 3

Arg Val Glu Phe Asn Glu Asp Gly Asp Arg Ser Tyr Ile Pro Glu Ala
1               5                   10                  15

Lys Ala Ser Cys Tyr Gly
            20
```